United States Patent [19]

Braun et al.

[11] 4,316,470
[45] Feb. 23, 1982

[54] APPROXIMATOR FOR ANASTOMOTIC SURGERY

[75] Inventors: Karl Braun, Talheim; Erich Wintermantel, Tübingen, both of Fed. Rep. of Germany

[73] Assignee: Aesculap-Werke Aktiengesellschaft, vormals Jetter & Scheerer, Tuttlingen, Fed. Rep. of Germany

[21] Appl. No.: 101,679

[22] Filed: Dec. 10, 1979

[30] Foreign Application Priority Data

Dec. 27, 1978 [DE] Fed. Rep. of Germany ....... 2856386

[51] Int. Cl.³ ..................... A61B 17/00; A61B 17/04; A61B 17/08
[52] U.S. Cl. ............................... 128/346; 128/334 R; 128/335
[58] Field of Search ........... 128/346, 325, 326, 334 R, 128/334 C, 335, 20, 352, 353; 269/226, 252

[56] References Cited
U.S. PATENT DOCUMENTS 2,768,664 10/1956 Morgan ............................... 269/226
4,156,424 5/1979 Burgin ................................. 128/20
4,165,747 8/1979 Bermant ......................... 128/334 C

FOREIGN PATENT DOCUMENTS 2730691 1/1978 Fed. Rep. of Germany ...... 128/325
2713093 9/1978 Fed. Rep. of Germany ... 128/334 R
1081863 12/1954 France .................................. 128/20
395074 1/1972 U.S.S.R. .......................... 128/334 C Primary Examiner—Robert W. Michell
Assistant Examiner—C. W. Shedd
Attorney, Agent, or Firm—Martin A. Farber

[57] ABSTRACT

An approximator for anastomotic surgery having two parallel guide bars connected rigidly at one end to a fixed clamp holder. Another clamp holder is displaceably guided on the guide bars. One of the guide bars is a meshing bar non-rotatably mounted to the fixed clamp holder. A driver is mounted on the displaceable clamp holder rotatably about an axis crossing the longitudinal axis of the meshing bar and is formed with a toothed gear engaging the driving bar, the latter and the toothed gear forming a rack and pinion gearing.

13 Claims, 8 Drawing Figures

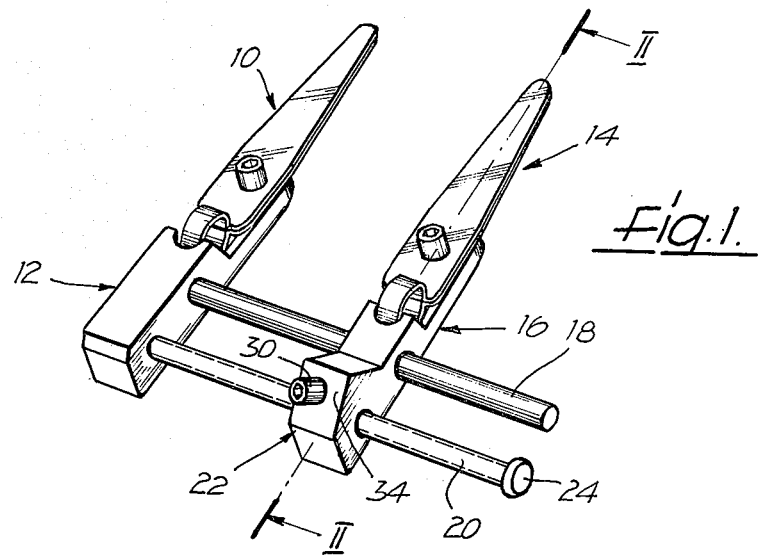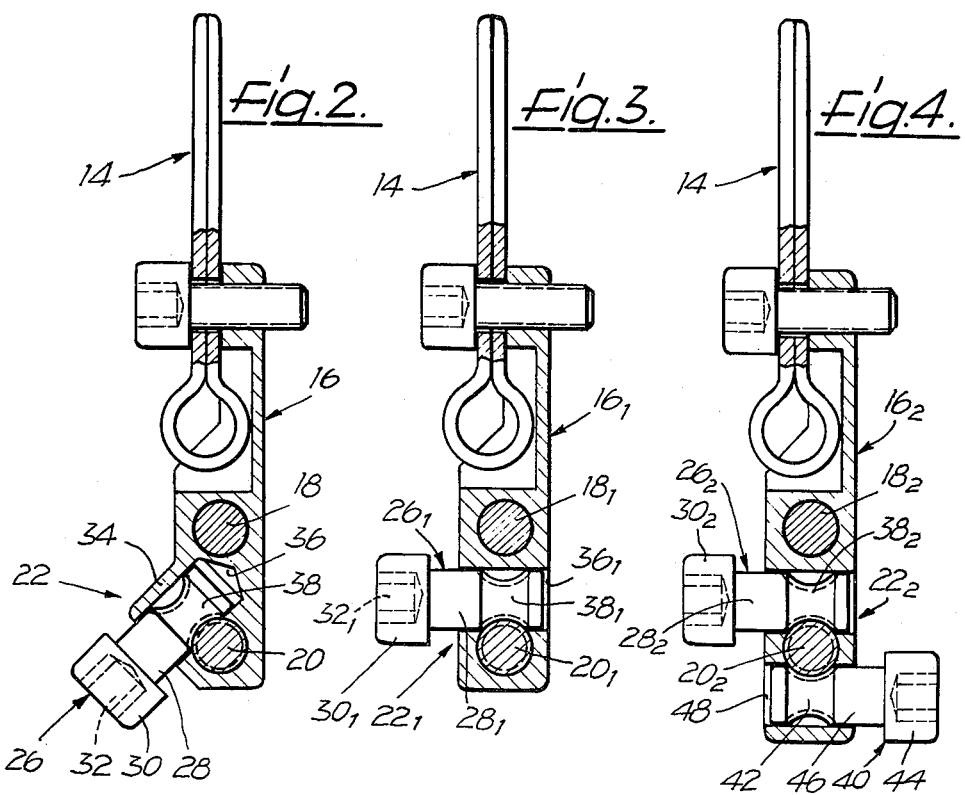

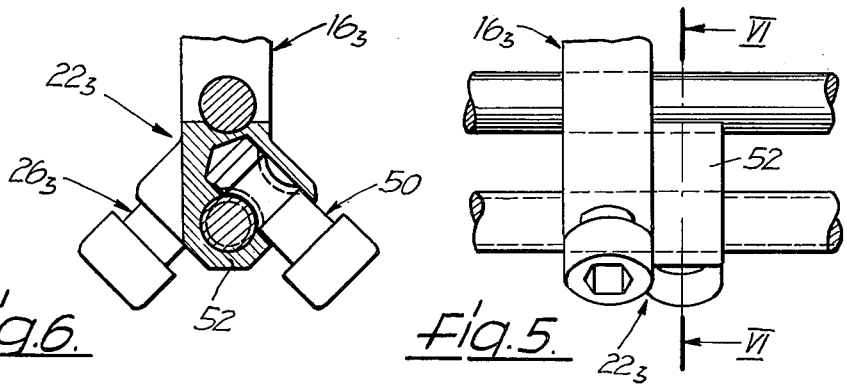
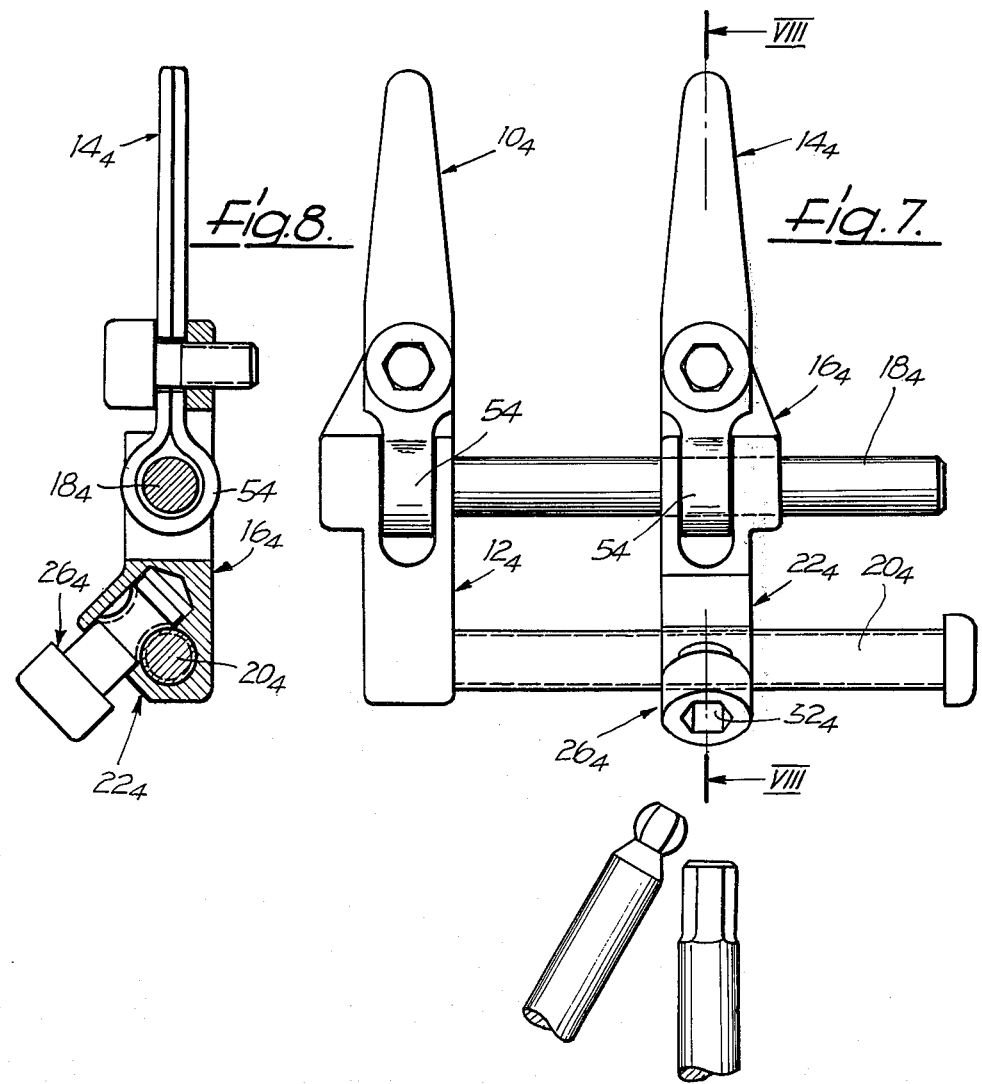

APPROXIMATOR FOR ANASTOMOTIC SURGERY

This invention relates to an approximator having two parallel guide bars which are connected to each other rigidly by a first clamp holder arranged on one end and by a displaceable second clamp holder which is guided on both bars; having a driving bar which is similar to a rack and is arranged parallel to one of the two guide bars and supported at the end on the fixed clamp holder and passes through the displaceable clamp holder; having a driver which acts on the driving bar and by the rotation of which around its longitudinal axis the movable clamp holder is displaceable; and having two clamps which are arranged on their holders and each of which has a jaw which is movable relative to the other.

In one approximator of this type known from German GS No. 7 632 903, the driving bar and the driver are a threaded spindle and a rotary handle fastened to the one end of said spindle, respectively. The threaded spindle, at its other end facing away from the rotary handle, is rotatably mounted on the stationary clamp holder and threaded through the displaceable clamp holder with which it forms a helical gearing. The driving rod extends centrally through the space between the two guide bars, parallel to the latter. Accordingly, the turnable handle is located on the end outside of this intermediate space.

The known approximator has the disadvantage that it is too expensive in construction and has too great a length in the direction of the displacement of the second clamp holder. Another disadvantage is that the driving rod, in order to produce a self-locking action, must be a threaded spindle of very slight pitch, this pitch requiring a relatively large angle of rotation of the driver for a given displacement of the second clamp holder, which is time consuming.

The object of the present invention therefore is to create an approximator which does not have these disadvantages, is simpler and cheaper, and can be made in smaller size and displaceable by smaller turning movements without the precision of the adjustment of the displaceable clamp being greatly impaired by this.

This object is achieved in accordance with the invention, starting from an approximator of the aforementioned type, in the manner that the meshing bar forms the other guide bar i.e., one of said two-guide bars, and is non-rotatably mounted on the stationary clamp holder; that the driver is mounted for rotation on the displaceable clamp holder around an axis which intersects with the longitudinal axis of the meshing bar and that it has a spur gear; and that the meshing bar and the spur gear form a rack-and-pinion gear.

In this way the result is advantageously obtained that of the three bars of the known approximator one is done away with, the driver is not arranged on the end but on the side, and the rack-and-pinion gearing permits rapid approximation due to its high transmission ratio.

One preferred embodiment of the approximator of the invention whose meshing bar is developed as in the known approximator and, as mentioned, as a threaded spindle of slight pitch similar to a round rack, is characterized by a globoidal spur gear of its rack-and-pinion gearing, in particular one with oblique teeth. The globoid as basic body of the spur gear surrounds by its arcuate concave generatrix a part of the periphery of the meshing bar and thereby automatically prevents an undesired displacement of the driver in the direction of its longitudinal axis and axis of rotation.

In the preferred embodiment, a stop member for the displaceable clamp holder is fastened to the free end of the threaded spindle which is used as the meshing bar. The stop member, when removed, makes it possible for the displaceable clamp holder to come into engagement with the free end of the threaded spindle and, when the stop member is placed on, it sees to it that such second clamp holder, at the maximum distance apart of the clamps, does not unintentionally come out of engagement with the threaded spindle.

In the preferred embodiment, the driver engages transversely into the space between the two guide bars, therefore between the one guide bar and the threaded spindle. In this way the required minimum distance apart of the two guide bars is spatially utilized in order to keep the approximator as small as possible transverse to the direction of displacement.

In the preferred embodiment, the driver has a shaft which is arranged in a blind bore hole in the displaceable clamp holder, the globoidal spur gear being developed in said shaft, and it also has a head bearing a drive means for a rotary key. This development of the driver is extremely suitable since it combines attack, support and engagement in compact manner.

In one variant of the preferred embodiment having known pincers with backs (in the form of circular rings) as clamps, the backs of the two clamps are arranged on one of the two guide bars so that the structural length of the approximator transverse to the direction of displacement is relatively small.

In the preferred embodiment, the two guide bars form an acute angle with each other so that the distance apart of their free ends at the end of the path of displacement on the outside is greater than the distance apart at the stationary part. Accordingly, the adjustment of the displaceable clamp within the range of displacement of its clamp holder is more reliable while still assuring sufficient precision since in this region the friction of the displaceable clamp holder on the two guide bars is increased.

One advantageous variant of the embodiment is characterized by two crossed drivers which are accessible from the side facing away from the clamp on the displaceable holder. This further development and form of the approximator of the invention makes it possible for the operator, who is working under a microscope, to actuate the driver obliquely from in front with the approximator horizontal even if it is turned. Furthermore optionally one of the two drivers can be actuated without coming too close to the clamp associated with it. Many variants are of course possible with respect to the number and arrangement of the drivers some of which will be shown.

The invention is explained in detail below with reference to the preferred embodiment of the approximator of the invention shown by way of example in the drawing and to four variants thereof.

FIG. 1 is a perspective view of the first embodiment;

FIG. 2 is a section along the Line II—II of FIG. 1 through the embodiment;

FIG. 3 is a section corresponding to FIG. 2 through a first variant of the embodiment;

FIG. 4 is a section corresponding to FIG. 2 through a second variant of the embodiment FIG. 5 is a view, broken away, of a third variant of the embodiment;

FIG. 6 is a section along the Line VI—VI of FIG. 5 through the embodiment shown in that figure;

FIG. 7 is a top view of a fourth variant of the embodiment in combination with two different rotary keys; and FIG. 8 is a section corresponding to FIG. 2 through the fourth variant.

The embodiment shown in FIGS. 1 and 2 comprises essentially a first clamp 10, a first clamp holder 12, a second clamp 14, a second clamp holder 16, two guide bars 18 and 20 and a displacement device 22.

The two clamps 10 and 14 are of the type described in German GS No. 7 709 313 (FIGS. 1-3) and are arranged on the clamp holders 12 and 16 approximately in the manner described therein, so that further explanation is unnecessary.

The first clamp holder 12, which is to be considered stationary, is fastened to two adjacent ends of the two guide bars 18 and 20 so that these bar ends are rigidly connected with each other. The second clamp holder 16 is displaceably supported on the two guide bars 18 and 20 by means of two smooth bore holes. Of the two parallel guide bars the guide bar 18 which lies closest to the clamps 10 and 14 is a smooth round bar and the guide bar 20 which lies further away is a threaded spindle of slight pitch. On the free end of this threaded spindle 20 there is fastened a stop 24 which has the shape of a circular disc and which enters into action when the two clamps 10 and 14 have reached their maximum distance apart.

The displacement device 22 for the displacement of the second clamp 14 in a plane defined by the two clamps parallel to the plane determined by the two guide bars 18 and 20, first of all comprises the threaded spindle 20 as a meshing bar and furthermore a driver 26. The latter comprises a shaft 28 of originally circular cylindrical surface and a head 30 having a driving means 32 in the form of a hexagon socket. The shaft 28 at its free end remote from the head 30 engages in oblique position between the two guide bars 18 and 20. For this purpose the second clamp holder 16 is provided with a shoulder 34 which is triangular as seen in section in FIG. 2, and it is provided with an oblique blind hole 36 which passes through the shoulder 34 and terminates between the two guide bars 18 and 20. The blind hole 36 receives the shaft 28 of the driver 26 with slight play. Within the shaft 28 there is developed a globoidal spur gear 38 which interrupts its circumferential surface, the pitch of said spur gear being adapted to the thread of the guide bar 20. The spur gear 38 meshes with the teeth of the threaded spindle 20 which lie opposite to it.

Due to the fact that the spur gear 38 has, as its basic body, a globoid which partially surrounds the guide bar 20, the driver 26 is held, without any additional measure, in the blind hole 36. When the second clamp holder 16 is placed onto the free ends of the two guide bars 18 and 20, of which guide bars the threaded spindle 20 still does not bear the stop member 24, the driver 26 is held in position until the threaded spindle 20 comes into engagement with its spur gear 38. The tooth thickness on the spur gear 38 should increase continuously from the smallest diameter up to the largest diameter of the spur gear so that when the driver 26 is placed under axial load by a rotary key which engages into the drive means 32 the play is reduced in the rack-and-pinion gearing which is formed by the meshing bar 20 and the spur gear 38 of the driver 26.

For the displacement of the second clamp 14 relative to the first clamp 10 the driver 26 need merely be turned in the desired direction in order for the displacement device 22 to enter into action. A locking of the second clamp holder 14 in the position reached after the displacement is not necessary since the aforementioned rack-and-pinion gearing has sufficient self-locking inherent in it.

In the first variant of the embodiment, shown in FIG. 3, the shoulder 34 on the second clamp holder $16_1$ has been dispensed with and the driver $26_1$ of the displacement device $22_1$ is so arranged in a continuous open ended bore hole $36_1$ that its longitudinal axis passes perpendicularly through the plane defined by the longitudinal axes of the two guide bars $18_1$ and $20_1$.

The second variant of the embodiment is derived from the first embodiment and has, as shown in FIG. 4, a second driver 40 whose globoidal spur gear 42 lies diametrically opposite the spur gear $38_2$ of the driver $26_2$ with reference to the meshing bar $20_2$. For this purpose, the two drivers $26_2$ and 40 are arranged parallel to each other but with their heads $30_2$ and 44 lying on opposite sides of the second clamp holder $16_2$. The shaft 46 of the second driver 40 engages in a continuous bore hole 48 in the extended clamp holder $16_2$.

The third variant of the embodiment is, as shown in FIGS. 5 and 6, a combination of the embodiment of FIG. 2 with the second variant in accordance with FIG. 4. Accordingly, the displacement device $22_3$ in this case has two drivers $26_3$ and 50 which are crossed askew at right angles. For the second driver 50 the displaceable clamp holder $16_3$ has a lateral holding part 52.

The fourth variant of the embodiment differs from this substantially only by the fact that, as shown in FIGS. 7 and 8, the two clamp holders $12_4$ and $16_4$ are made shorter and the two backs, (having the shape of circular rings) 54 of the clamps $10_4$ and $14_4$ which are developed as pincers are seated with ample play on the round bar $18_4$. From FIG. 7 it can be seen that for engagement in the drive means $32_4$ of the driver $26_4$ a rotary key with cylindrical head or spherical head can be used. The spherical head permits an oblique holding of the rotary key, which may be necessary depending on the circumstances of the operation.

We claim:

1. An approximator, comprising
   two spaced guide bars substantially parallel to each other defining a space therebetween,
   a first clamp holder connected rigidly to a first end of said two guide bars,
   a second clamp holder displaceably guided on said two guide bars,
   two clamps, having jaws respectively movable relative each other, mounted on said first and second clamp holders, respectively, one of said clamps mounted in said second clamp holder defining a plane of displacement by displacement of the latter,
   one of said two guide bars constitutes a meshing bar non-rotatably connected to said first clamp holder constituting the first-mentioned rigid connection of the first clamp holder to said first end, and
   at least one driver being mounted on said second clamp holder rotatably about an axis crossing the longitudinal axis of said meshing bar and penetrating said plane of displacement of said one clamp, said driver is formed with a toothed gear operatively engaging with said meshing bar, the latter and said toothed gear forming a rack and pinion gearing.

2. The approximator as set forth in claim 1, wherein said meshing bar is a threaded spindle, said toothed gear is formed with teeth which are concave along the gear periphery.

3. The approximator as set forth in claim 2, wherein said toothed gear has inclined teeth.

4. The approximator as set forth in claim 2, further comprising stop means for stopping displacement of said second clamp holder is fastenable to a free end of said threaded spindle, the latter constituting said meshing bar.

5. The approximator as set forth in claim 2, wherein said second clamp holder is formed with a blind bore, said driver includes, a shaft disposed in said blind bore, said toothed gear is formed on said shaft, a head having drive means for turning said head by a rotary key adapted to said drive means and being operatively connected to said shaft.

6. The approximator as set forth in claim 1, wherein said driver engages transversely into said space between said two guide bars.

7. The approximator as set forth in claim 1, wherein said clamps constitute two pincers, each of said pincers having a circular ring connecting said jaws remotely from two free gripping ends of the jaws, said ring is disposed on the other of said two guide bars, said other guide bar being parallel to said one of said two guide bars.

8. The approximator as set forth in claim 1, wherein said clamps and said jaws extend toward one side of said two guide bars, said jaws lying in a plane substantially parallel to a plane passing through the longitudinal axes of both of said two guide bars, said at least one driver includes two crossed drivers which are mounted and accessible on said second clamp holder adjacent the other side of said two guide bars.

9. The approximator as set forth in claim 9, wherein said two crossed drivers engage said meshing bar on diametrically opposite sides of said driving bar.

10. The approximator as set forth in claim 1, wherein said clamp holders have longitudinal axes exclusively extending crosswise to the parallel direction of said guide bars.

11. The approximator as set forth in claim 1, wherein said second clamp holder is directly displaceably mounted on said two guide bars and directly connected to said one clamp.

12. The approximator as set forth in claim 1, wherein said second clamp holder is formed with two parallel openings, said two guide bars extend through said two parallel openings respectively displaceably therein relative to said second clamp holder.

13. The approximator as set forth in claim 1, wherein said rack and pinion is self-lockable in any position.

* * * * *

UNITED STATES PATENT AND TRADEMARK OFFICE
CERTIFICATE OF CORRECTION

PATENT NO. : 4,316,470
DATED : February 23, 1982
INVENTOR(S) : Karl Braun, et al It is certified that error appears in the above-identified patent and that said Letters Patent are hereby corrected as shown below:

Column 6, Line 13,

"9," should read --8,--

Signed and Sealed this

Fourth Day of May 1982

[SEAL]

Attest:

Attesting Officer

GERALD J. MOSSINGHOFF

Commissioner of Patents and Trademarks